United States Patent [19]

Zoeller et al.

[11] Patent Number: 5,175,363
[45] Date of Patent: Dec. 29, 1992

[54] METHOD FOR PURIFICATION OF CARBOXYLIC ACIDS AND ANHYDRIDES

[75] Inventors: Joseph R. Zoeller; Regina M. Moncier, both of Kingsport, Tenn.

[73] Assignee: Eastman Kodak Company, Rochester, N.Y.

[21] Appl. No.: 646,029

[22] Filed: Jan. 28, 1991

[51] Int. Cl.$^5$ .............................. C09F 5/10; C11B 3/00
[52] U.S. Cl. .................................. 562/608; 562/606; 562/898
[58] Field of Search ................. 562/606, 608, 898

[56] References Cited

U.S. PATENT DOCUMENTS

| | | | |
|---|---|---|---|
| 3,950,365 | 4/1976 | Singer et al. | 260/419 |
| 4,020,114 | 4/1977 | Rescalli et al. | 260/681.5 R |
| 4,189,442 | 2/1980 | Lubsen et al. | 260/428.5 |
| 4,313,016 | 1/1982 | Manning | 585/832 |

FOREIGN PATENT DOCUMENTS 62-246536 10/1987 Japan .

OTHER PUBLICATIONS

Chemical Abstracts, 71649q, vol. 78, 1973.

Primary Examiner—Arthur C. Prescott
Assistant Examiner—V. Garner
Attorney, Agent, or Firm—Bernard J. Graves, Jr.; William P. Heath, Jr.

[57] ABSTRACT

Disclosed is a method for reducing olefinic impurities in solutions of carboxylic acids and/or anhydrides. The invention is especially useful for removing substantially all, i.e., greater than 90 percent of trace amounts of olefinic impurities.

12 Claims, No Drawings

METHOD FOR PURIFICATION OF CARBOXYLIC ACIDS AND ANHYDRIDES

FIELD OF THE INVENTION

This invention belongs to the field of synthetic organic chemistry. More particularly, it relates to a method for purifying carboxylic acids and anhydrides.

BACKGROUND OF THE INVENTION

Traces of olefinic impurities are often found in carboxylic acids or their anhydrides. These olefinic impurities are either introduced as a result of their application and recycle or as a consequence of their method of manufacture.

As a point of illustration, long chain saturated carboxylic acids generally contain small quantities of the olefin from which they were generated. For example, nanoic (C9) acid generated by hydroformylation and oxidation might contain 1-octene. These olefins are difficult to separate and, generally speaking, the low levels (ca. <100 ppm) of these olefinic impurities are tolerated commercially in the longer chain carboxylic acids. However, when subsequently used to generate carboxylic anhydrides by the exchange of acetic anhydride, the acetic acid by-product is also contaminated with the olefin. This problem is compounded by the fact that these olefins commonly distill as azeotropes (i.e., as azeotropic pairs) with the acetic acid.

As a further example, during the production or coproduction of acetic acid and acetic anhydride via the carbonylation of methyl acetate, acetone is generated as a by-product. This acetone by-product leads to the generation of mesityl oxide and 3-methyl butenoate derivatives by a condensation reaction.

These by-products may be difficult to remove. Generally, these small quantities of olefin might be regarded as unimportant. However, a critical parameter in achieving commercial grade carboxylic acids, particularly for C2 through C4 carboxylic acids, is the so-called "substances reducing permanganate" test. This test is adversely affected by the presence of these olefinic contaminants and reductions in the olefin level are often required when highly pure, or at least olefin-free, carboxylic acids and anhydrides are desired.

SUMMARY OF THE INVENTION

The present invention provides a method for reducing the amount of olefinic impurity in solutions comprising $C_2$–$C_8$ carboxylic acids and/or a $C_4$–$C_{16}$ anhydrides which comprises contacting said solution with a strongly acidic resin. The present invention is particularly useful for removing trace amounts of such olefinic impurities, thus providing $C_2$–$C_8$ carboxylic acids and $C_4$–$C_{16}$ anhydrides of exceptional purity.

DETAILED DESCRIPTION OF THE INVENTION

A standard test for detecting the presence of olefins in a mixture, in this case, carboxylic acids or anhydrides, is the so-called "substances reducing permangenate" test. If olefinic contaminates are present, they can be detected by monitorization of the extent of permangenate ($MnO_4^-$) reduction (i.e., olefin oxidation).

We have found that when carboxylic acids or solutions of carboxylic acids and anhydrides which are contaminated with olefinic impurities are heated in the presence of a strongly acidic resin, for example, Amberlyst ®-15 or Dowex ® 50 brand resins, which contain sulfonic acid residues, the olefinic impurity is suppressed or eliminated. This process has been shown to be effective in removing several olefins and there does not appear to be any noticeable limitation with regard to the structure of the olefin. For example, in the cases of 1-octene, mesityl oxide, and ethyl 3-methyl 2-butenoate, >90% of the olefin was removed.

The process is preferably run at elevated temperatures, i.e., about 25° C. to 200° C., most preferably from about 75° C. to 175° C., but removal can be demonstrated, albeit at lower efficiency, at lower temperatures. For example, at room temperature, 10% of the mesityl oxide present in an acetic acid solution can be removed in 3 hours and it is believed that, given sufficient time, the reaction will proceed to completion. The upper temperature limit for the process is established by the resin stability and typically should not exceed 175° C. and absolutely should not exceed a maximum of 220° C. at which point complete degradation of the resin is likely to occur.

Thus, the present invention provides a method for reducing the amount of olefinic impurities in a solution comprising $C_2$–$C_8$ carboxylic acids and/or $C_4$–$C_{16}$ anhydrides, which comprises contacting said solution with a strongly acidic resin.

Preferably, the strongly acidic resin is a resin which contains a multiplicity of sulfonic acid functional groups, said resin preferably being bound or grafted to a polymer "backbone", e.g., polystyrene. Examples of such resins are commercially available under the tradenames Dowex ® 50, Amberlyst ®-15, Amberlite ® IR-118, Amberlite ® IR-120, Amberlyst ® XN-1010, Amberlite ® IRP-69, and Nafion ®. (See, for example, Aldrich Chemical Co. Catalogue 1989–1990, Milwaukee, Wis.)

As noted above, the present invention is useful for reducing olefinic impurities from solutions comprising $C_2$–$C_8$ carboxylic acids and/or $C_4$–$C_{16}$ anhydrides. Examples of $C_2$–$C_8$ carboxylic acids and/or $C_4$–$C_{16}$ anhydrides include acetic acid, propanoic acid, n-butanoic acid, isobutyric acid, acetic anhydride, n-butyric anhydride, isobutyric anhydride, valeric anhydride, and the like. The present invention is especially useful in reducing olefinic impurities in acetic acid or acetic anhydride and mixtures thereof. The present invention is most useful when the olefinic contaminant is a $C_2$ to $C_{20}$ contaminant and is present in a concentration of about 50 parts per million (ppm) to about 1000 ppm. Generally speaking, it is possible to reduce trace olefinic impurities in such a solution to a level of about 0–20 ppm.

As used herein, the term $C_2$–$C_{20}$ olefinic contaminant refers to any $C_2$ to $C_{20}$ hydrocarbon containing at least one carbon-carbon double bond and optionally containing one or more heteroatoms. Examples of such contaminants includes ethylene, propene, butene, butadiene, mesityl oxide, 1-octene, 5-pentenoic acid, and the like. As an especially preferred embodiment, the amount of mesityl oxide contaminant in acetic acid and/or acetic anhydride is reduced through the practice of the present invention.

EXPERIMENTAL SECTION

Example 1

A 100 g sample of acetic acid contaminated with 221 ppm of 1-octene was added to a 250 mL round bottomed flask containing 1.0 g of Amberlyst ®-15 brand resin. The mixture was stirred and heated at reflux for 3 hours. The mixture was then cooled to room temperature. Analysis for 1-octene indicated that only 15 ppm of 1-octene remained. (% olefin removed: 93%)

Example 2

A 100 g sample of acetic acid contaminated with 351 ppm of ethyl 3-methyl-2-butenoate was added to a 250 mL round bottomed flask containing 1.0 g of Amberlyst®-15 brand resin. The mixture was stirred and heated at reflux for 3 hours. The mixture was then cooled to room temperature. Analysis for ethyl 3-methyl-2-buteneoate indicated that there was no ethyl 3.methyl-2-butenoate remaining. (% olefin removed: 100%)

Example 3

A 100 g sample of acetic acid contaminated with 293 ppm of mesityl oxide (4-methyl-3-penten-2-one) was added to a 250 mL round bottomed flask containing 1.0 g of Amberlyst®-15 brand resin. The mixture was stirred and heated at reflux for 3 hours. The mixture was then cooled to room temperature. Analysis for mesityl oxide indicated all the mesityl oxide had been consumed. (% olefin removed: 100%)

Example 4

100 g sample of acetic acid contaminated with 146 ppm of mesityl oxide was added to a 250 mL round bottomed flask containing 1.0 g of Dowex®-50X2-200 brand resin. The mixture was stirred and heated at reflux for 3 hours. The mixture was then cooled to room temperature. Analysis for mesityl oxide indicated 13 ppm of mesityl oxide remained. (% olefin removed: 91%)

Example 5

A 100 g sample of acetic acid contaminated with 284 ppm of mesityl oxide was added to a 250 mL round bottomed flask containing 1.0 g of Amberlyst®-15 brand resin. The mixture was stirred at room temperature for 3 hours. Analysis for mesityl oxide indicated that 255 ppm of mesityl oxide remained. (% olefin removed: 10%) This example indicates the need for higher reaction temperatures or longer reaction times to attain desired rates/amounts of olefin removal. Examples 6 and 7 demonstrate the utility of carboxylic acid/anhydride mixtures in this process as well as the drawback of generating β-diketones.

Example 6

A 100 g sample of a 1:1 (wt.:wt.) acetic anhydride:acetic acid solution contaminated with 289 ppm of mesityl oxide was added to a 250 mL round bottomed flask containing 1.0 g of Amberlyst®-15 brand resin. The mixture was stirred and heated at reflux for 3 hours. The mixture was then cooled to room temperature. Analysis for mesityl oxide indicated that all of the mesityl oxide had been consumed. However, additional analysis revealed that, whereas there was no 2,4-pentanedione in the initial solution, the treated sample now contained 297 ppm of 2,4-pentanedione. (% olefin removal: 100%)

Example 7

A 100 g sample of a 3:2 (wt.:wt.) acetic anhydride:acetic acid solution contaminated with 86 ppm of mesityl oxide and 18.4 ppm of 2,4-pentanedione was added to a 250 mL round bottomed flask containing 1.0 g of Amberlyst®-15 brand resin. The mixture was stirred and heated at reflux for 3 hours. The mixture was then cooled to room temperature. Analysis for mesityl oxide indicated that 6 ppm mesityl oxide remained. (% olefin consumed: 93%) The level of 2,4-pentanedione at the end of the experiment had risen to 177 ppm.

Control Example For Mesityl Oxide Removal

A 100 g solution of 1:1 (wt.:wt.) acetic acid - acetic anhydride containing approximately 300 ppm of mesityl oxide was prepared. A sample of the initial solution was analyzed by gas chromatography and determined to contain mesityl oxide in a concentration of 294 ppm. The solution was heated at reflux for 3 hours and then analyzed again for mesityl oxide by gas chromatography and determined to have 266 ppm of mesityl oxide; in other words, 10% of the olefinic impurity (mesityl oxide) was consumed through thermal decomposition.

We clam:

1. A method for removing trace amounts of monoolefinic impurities in a solution comprising a $C_2$–$C_8$ carboxylic acid and/or a $C_4$–$C_{16}$ anhydride, which comprises contacting said solution with a strongly acidic resin.

2. The method of claim 1, wherein the olefinic impurity is a $C_2$ to $C_{20}$ hydrocarbon containing one carbon-carbon double bond.

3. The method of claim 1, wherein the olefinic impurity is mesityl oxide.

4. The method of claim 3, wherein the solution comprises acetic acid.

5. The method of claim 1, wherein the solution comprises acetic anhydride.

6. The method of claim 1, wherein the solution comprises a mixture of acetic acid and acetic anhydride.

7. The method of claim 1, wherein the solution comprises n-propanoic acid.

8. The method of claim 1, wherein the solution comprises n-butanoic acid.

9. The method of claim 1, wherein the solution comprises iso-butyric acid.

10. The method of claim 1, wherein the solution comprises propanoic anhydride.

11. The method of claim 1, wherein the solution comprises butanoic anhydride.

12. The method of claim 1, wherein the solution comprises isobutanoic anhydride.

* * * * *